United States Patent [19]

Paikoff

[11] Patent Number: 4,522,302
[45] Date of Patent: Jun. 11, 1985

[54] PRE-STERILIZED MEDICAL PROCEDURE KIT PACKAGES

[75] Inventor: Myron Paikoff, Colonie, N.Y.

[73] Assignee: Sterling Drug Inc., New York, N.Y.

[21] Appl. No.: 586,362

[22] Filed: Mar. 5, 1984

[51] Int. Cl.³ .................. B65D 1/34; B65D 77/04; B65D 83/04
[52] U.S. Cl. .................................. 206/570; 206/210; 206/571; 206/364; 422/34
[58] Field of Search ............... 206/207, 210, 363, 364, 206/367, 370, 438, 484.1, 484.2, 440, 570, 571, 572; 422/34, 300, 302

[56] References Cited

U.S. PATENT DOCUMENTS

| | | | |
|---|---|---|---|
| 659,058 | 10/1900 | Edlem | 206/572 |
| 2,947,415 | 8/1960 | Garth | 206/364 |
| 3,770,119 | 11/1973 | Hultberg et al. | 206/439 |
| 3,801,278 | 4/1974 | Wagner et al. | 422/300 |
| 3,815,315 | 6/1974 | Glick | 422/34 |
| 3,851,649 | 12/1974 | Villari | 206/571 |
| 3,926,309 | 8/1975 | Center | 206/364 |
| 3,954,174 | 5/1976 | Kraus | 206/572 |
| 3,967,728 | 7/1976 | Gordon et al. | 206/364 |
| 4,085,845 | 4/1978 | Perfect | 206/363 |
| 4,128,173 | 12/1978 | Lazarus et al. | 206/570 |
| 4,149,635 | 4/1979 | Stevens | 206/370 |
| 4,153,160 | 5/1979 | Leigh | 206/37 D |
| 4,405,047 | 9/1983 | Barba | 206/570 |
| 4,444,310 | 4/1984 | Odell | 206/526 |

FOREIGN PATENT DOCUMENTS 8101545  6/1981  PCT Int'l Appl. ................. 206/572

Primary Examiner—William T. Dixson, Jr.
Assistant Examiner—Brenda J. Ehrhardt
Attorney, Agent, or Firm—William G. Webb; B. Woodrow Wyatt; Paul E. Dupont

[57] ABSTRACT

This invention provides medical procedure packages comprising a pre-sterilized kit within an outer package wrap, the package being so designed that all components of the package are sterilized using sterilization methods which are compatible with the chemical compositions of the components and their stability to such sterilization methods, and wherein the internal sterility of the package is maintained from final package sealing until the package is delivered to a sterile operating room environment.

5 Claims, 4 Drawing Figures

PRE-STERILIZED MEDICAL PROCEDURE KIT PACKAGES

RELATED APPLICATIONS

Paikoff, Hadtke and Hain U.S. application Ser. No. 586159 filed Mar. 5, 1984, discloses and claims certain unitary, two-compartment medical procedure package kits containing, in one compartment thereof, certain medical procedure components and, in the other compartment, a medicament containing vial. The kits are so-structured that, although all the elements of the kits, except the vial, are compatible with, and are sterilized by, ethylene oxide, while the medicament-containing vial is compatible with and is sterilized by heat, the various components can be separately sterilized, as required by their respective sterilization compatibilities, and then combined before final packaging in a package whose interior is completely sterile and can be so-maintained until ultimate use of the package contents.

BACKGROUND

This invention relates to the field of sterile packaging of components to be used in certain medical operative procedures. More specifically, the invention relates to the packaging, in a single outer package, of various components used in such procedures where, because of the chemical nature of certain portions of some of the components, particular sterilization methods must be used with some of the components, while other different sterilization methods must be used with the others.

While the concept here-involved can be applied to the packaging of any medical procedure package requiring the inclusion of any medicament-containing vial which is conventionally sealed with a rubber closure plug or diaphragm, the packages provided by the present invention have particular use in X-ray radiographic procedures, such as myelographic procedures, in which a radiopaque contrast agent is injected into the spinal arachnoid space so as to provide X-ray visualization of the spinal chord. In such procedures, the skin area on the patient's spine where the injection is to be made is sterilized using appropriate sponge scrubbers and antibacterial agents. Then using a hypodermic syringe and a vial of local anesthetic, the area around the injection site is anesthetized. A spinal puncture needle is then inserted into the arachnoid space, and, if desired, samples of cerebro spinal fluid (CSF) are withdrawn by attachment of a cannula fitted with a male tapered joint on one end for attachment of the cannula to the puncture needle and a female tapered joint on the other end for attachment of the cannula to a hypodermic syringe, the samples being collected in small graduated sample tubes. The radiopaque solution is then withdrawn from a vial containing the same, conventionally sealed with a rubber plug, by puncturing the plug with a separate hypodermic needle and aspirating the solution into a syringe. The syringe is then disconnected from the aspirating needle, attached either directly to the puncture needle in the patient's spine or to the cannula attached to the needle, and the radiopaque medium is then injected into the arachnoid space. When the examination is complete, the puncture needle is withdrawn, leaving the radiopaque medium in place to be metabolized by the body, or, alternatively, the medium is removed by aspiration and then the puncture needle is withdrawn.

It will be clear from the above description that each of the various essential medical procedure components used in the myelographic procedure, including sponge scrubbers, local anesthetic syringe and vial, puncture needles with associated needle sheaths and closure caps, cannulas and associated closure caps, sample tubes, contrast agent vial and injection syringe, as well as miscellaneous items such as drapes to cover the patient and gauze pads for blotting fluids around the injection site during the procedure, must all be pre-sterilized before or during packaging and, most importantly, must be maintained in a sterile condition until used. The conventional approach to the problem of ensuring sterility in each of the components, some of which are typically made of plastic materials, has been to provide all the components, except the vial of contrast agent, in one package unit, such as a plastic tray typically made of polystyrene foam or thermoformed polystyrene, the vial of contrast agent being supplied in a separate package. This separation of the vial of contrast agent from the remainder of the package contents is necessary, because the components stored and shipped in the plastic trays cannot be heat sterilized due to the instability of the plastics to heat. Thus the trays and their associated essential medical procedure components can only be sterilized by ethylene oxide gas. On the other hand, the vial of contrast agent, which, as stated, is conventionally sealed with a pierceable rubber plug, cannot be sterilized by ethylene oxide because of the known destructive effect the latter has on rubber. Thus the contrast agent vial can only be heat sterilized. The present invention provides a unique means for maintaining complete sterility of all the components used in the procedure while combining all the components, including the contrast agent vial, into a single package unit.

INFORMATION DISCLOSURE STATEMENT

Garth U.S. Pat. No. 2,947,415 discloses a plastic, heat-sealed package for holding medical and surgical items constructed of two layers of plastic, one of polyethylene, which is ethylene oxide permeable, and the other of Mylar, which the patentee states is gas impermeable. The packages are sterilized with ethylene oxide after sealing and packaging.

Hultberg et al. U.S. Pat. No. 3,770,119 discloses a sterile prepackaged tray containing pre-sterilized medical and surgical items needed to perform simple medical and surgical procedures such as liver biopsy or spinal anesthesia. The package comprises a tray, having compartments therein for holding medical and surgical items, and a drape sealed to the interior of the tray. When packaged for shipment, the drape is folded inside the tray, thus covering the tray contents. The entire assembly is then sealed with a gas-permeable, contamination-impermeable peelable sheet 14, sterilized with ethylene oxide or the like and then sealed. In use, the peelable sheet is removed, and the sterile drape is unfolded to provide a sterile field and to provide access to the tray and its contents.

Center U.S. Pat. No. 3,926,309 discloses a two-layer sterile package for two different articles. The package is so constructed that sequential access to the articles is provided without the necessity of disturbing the sterility of the second article when the first is removed. The first layer is a polyethylene envelope formed by folding the sides of a polyethylene sheet towards one another, leaving a space 16 between the edges thus forming a tube which is open along its side and at both ends, and then heat sealing the ends of the tube. The second layer is formed by heat sealing a gas-permeable, bacteria-impermeable paper over the first. The entire package is then gas sterilized and vacuum purged prior to shipment.

Gorden et al. U.S. Pat. No. 3,967,728 discloses a tandem type pouch package, one section of which holds a catheter, the other a lubricant. The package is constructed of inner layers of polyethylene and outer layers of a gas-impermeable metal, e.g. aluminum foil. The catheter package itself (11) is first gas sterilized with ethylene oxide and then placed within an outer envelope 40, likewise sterilized on the interior. The latter is then sealed.

Stevens U.S. Pat. No. 4,149,635 discloses kits for use in "milogram, arthrogram and angiogram" procedures. The kits provide unfoldable, strip trays in which various instruments needed for medical procedures are arranged sequentially in the package in the order in which the instruments would be needed in the particular procedure. The patentee states that sterilization of the package unit can be accomplished in "conventional ways such as by carbon dioxide or radiation sterilization".

Leigh U.S. Pat. No. 4,153,160 discloses a slide-stop tray kit for use in percutaneous transhepatic cholangiography (PTC) procedures. The kit is composed of an upper tray, the lower side of which slidably engages the upper section of a lower tray. The upper tray contains materials for establishing a sterile field, such as pre-moistened swabs or surgical drapes, and the lower tray contains instruments and the like which are necessary for the PTC procedure itself. The patentee states that "Prior to shipment, all of the instruments, materials, and both trays are sterilized, e.g. by ethylene oxide sterilization or the like. The sterilized instruments and materials can then be packaged in individual sterile packages . . . which are placed in the appropriate article supporting recesses."

None of these references, and so far as I am aware no other references, address the problem of the packaging of different components of sterile medical procedure packages, which require different means of sterilization for the components, in a single package unit.

BRIEF DESCRIPTION OF THE INVENTION

The package kits provided by the present invention successfully address the problem, not dealt with by the prior art, of providing, in a single sterile package, all the diverse, essential components, including a rubber closured vial of a medicament agent such as a radiopaque agent, required for use in medical procedures.

More specifically, the present invention is directed to medical procedure packages comprising a presterilized unit within an outer package wrap having a sterilized interior, the inner unit comprising an essentially unitary, two-compartment kit pre-sterilized by ethylene oxide and wrapped within an inner package wrap, one compartment of the kit containing essential medical procedure components which are compatible with, and after placement in said compartment are subjected to sterilization by, ethylene oxide, the second compartment of the two-compartment kit containing a rubber closured vial of medicament agent which is incompatible with ethylene oxide sterilization and which is heat sterilized separately and then sealed inside an ethylene oxide impermeable container which is placed in said second compartment prior to ethylene oxide sterilization of the entire kit and its contents.

BRIEF DESCRIPTION OF THE DRAWINGS

The invention is described below with reference to the accompanying drawings wherein.

DETAILED DESCRIPTION OF THE INVENTION

The invention will now be described in detail with reference to the foregoing drawings wherein like numerals are used to identify like parts.

Figure 3:
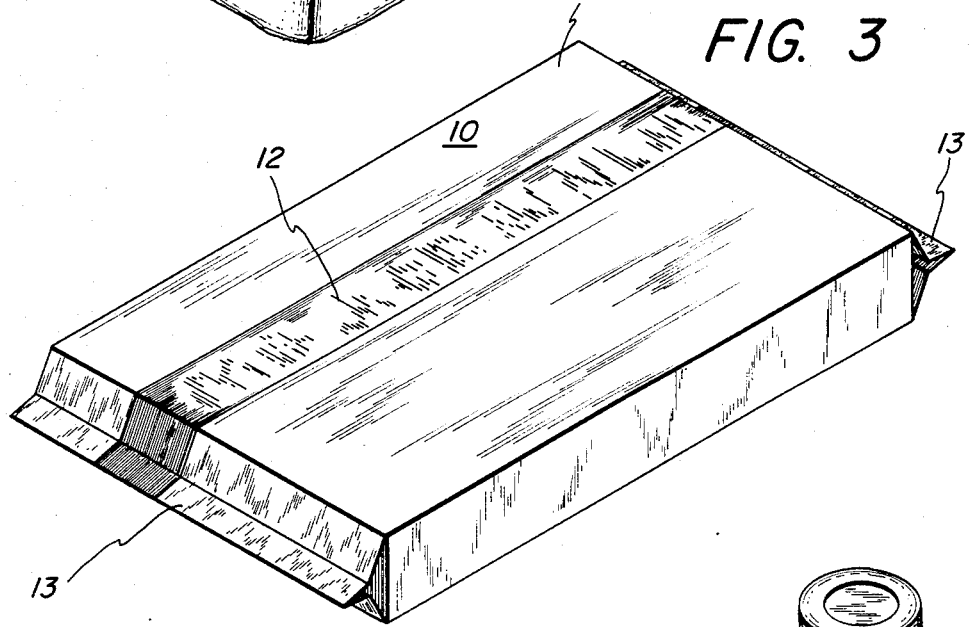
FIG. 3 is a perspective view of the package kit unit of FIGS. 1A and 1B as it would appear within an outer package wrap and as the package would be delivered, through commercial channels, to a doctor, a hospital or a clinic.

As stated before, this invention relates to presterilized package units comprising essentially a two-compartment kit, said presterilized units being shipped in commerce within an outer package wrap, the entire package, represented by general reference numeral 10, being shown in FIG. 3. The outer package wrap 11 consists of a suitable package material, such as plastic or preferably pasteboard, sealed around an inner package unit, to be described below with reference to FIGS. 1A and 1B. The outer wrap may bear printed matter 12 to indicate the nature of the package contents and the commercial origin of the package. The ends of the outer wrap contain flaps 13 which are sealed, for example, by heat or glue sealing.

In the packaging of sterile items, such as the medical procedure units of the present invention, it is required practice that the sterilized items be covered with four layers of a sterile hospital wrap, conventionally of paper. Thus the package units of the present invention, as they would be removed from the outer package wrap 11, would be wrapped within an inner package wrap 28, shown in FIG. 1A, in such a way, to be described below, as to provide the requisite four layers of hospital wrap over the open top of the inner package.

Figure 1A:
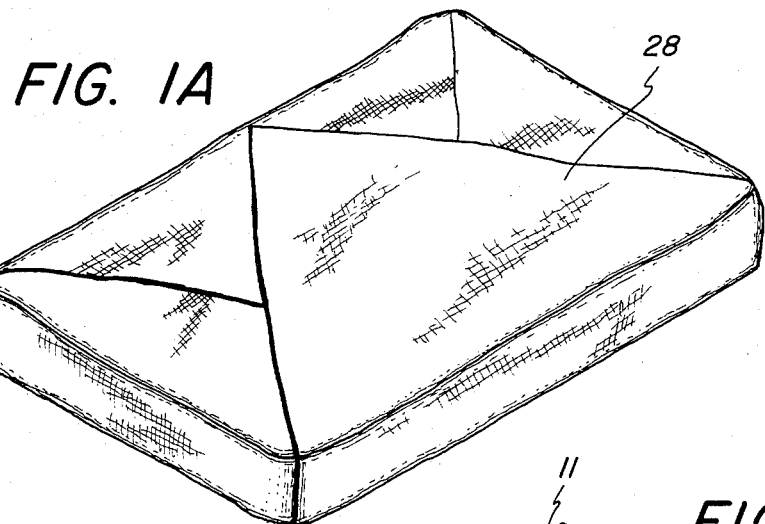
FIG. 1A is a perspective view of a pre-sterilized inner package unit of the invention as it would appear upon removal from an outer package wrap.
Figure 2:
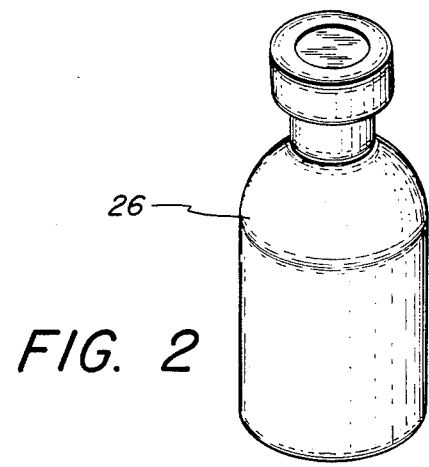
FIG. 2 is a perspective view of a medicament containing vial which is one of the elements contained within the package kit units of the present invention.
Figure 1B:
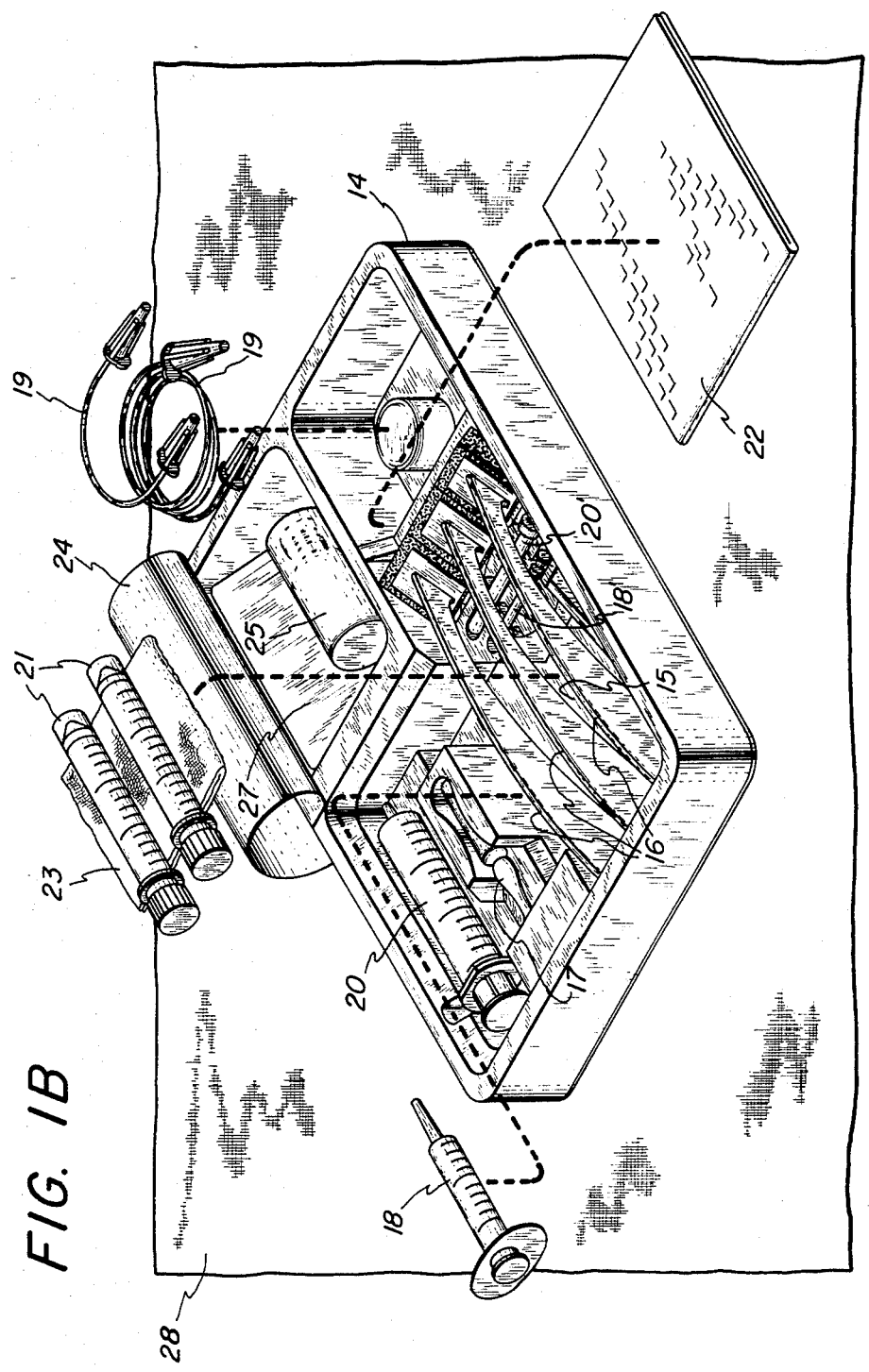
FIG. 1B is a perspective view of an inner package unit of FIG. 1A with an inner package wrap unfolded to show the open compartment containing a sealed metal can for holding a separately heat sterilized medicament containing vial, shown in phantom within the can.

The inner package unit, as it would appear when the inner package wrap described above is unfolded, is depicted in FIG. 1B. As shown in FIG. 1B, the inner package comprises a set-up tray 14, for example of molded or thermo-formed plastic having essentially two compartments. One compartment 15 is relatively large and is equipped with appropriate dividers or flexible holding means for storing various medical procedure components, such as scrubbing or cleansing means 16 comprising sponge scrubbers with attached handles, local anesthesia producing means 17 comprising a glass vial containing a local anesthetic, local anesthetic syringe injection means 18, local anesthetic syringe needle/sheath/cap 18', sampling or drug transfer means 19 comprising cannulas fitted with male and female tapered joints on either end, drug syringe injection means 20, drug syringe puncture needle/sheath/cap 20', and fluid sampling means 21. The kit may also contain folded patient covering means 22, such as a surgical drape, and swabbing/bandage means 23, such as folded gauze pads. The tray 14 is equipped with a separate, relatively small compartment 27 which may optionally be covered by a peelable covering 24, which is shown in a peeled back position in the figure. When the kit is needed for use, the peelable covering is removed to expose a sealed can 25 having a peel-off lid and containing a rubber closured medicament containing vial 26 such as depicted in FIG. 2 and shown in phantom inside the can in FIG. 1B.

In preparing the package unit for commercial use, vial 26 and open can 25 are first heat sterilized, and the vial is then sealed within the can. The various essential medical/surgical procedure components as described above are placed in their appropriate locations in large compartment 15 of the set-up tray, the sealed can is placed in its compartment, which is optionally sealed with a sterile barrier seal 24. Then the tray, containing all the essential medical/surgical procedure components 16–23, and the can/vial, is placed essentially in the center of a generally square piece of the inner package wrap material 28, the corners of the wrap are each in turn folded up over the open top of the tray, to thus provide the necessary four layers of inner wrap over the tray contents, the whole inner package thus wrapped, and as it would appear in FIG. 1A, is placed inside the outer package wrap 11, and the entire package is subjected to ethylene oxide sterilization. The ethylene oxide sterilizing gas is, of course, able to penetrate the outer package wrap and sterilize all the interior contents, including the set-up tray 14 and all of its contents, and especially the exterior of can 25. The gas however cannot penetrate the can, and so the previously heat sterilized vial 26, having an ethylene oxide sensitive rubber closure, is protected from the ethylene oxide gas.

In use, the entire package, including the outer package wrap, would be brought into the operating room and the outer package wrap opened. The inner, wrapped and sterile package unit containing the tray and medicament vial would be allowed to slide out of the outer package wrap onto a sterile surface. The inner package would then be opened, under sterile conditions, by folding back each of the four corners of the inner wrap, thus exposing the open tray and its contents, the unfolded inner wrap providing a sterile field for placement of each of the tray components as they are removed from the tray. The vial containing can is advantageously equipped with a conventional tear-off lid to permit easy opening and removal of the vial. It will be seen that when the packages of the invention are prepared and used as described above, the internal sterility of the packages and their contents is maintained from final package sealing until the packages are opened for use.

Although the invention has been described herein with particular reference to the application thereof to myelographic procedures and the various medical procedure components and medicament agent essential thereto, it will be understood that it is contemplated that the inventive concept here-involved can also be applied and adapted to any medical procedure which requires use of components or medicament vials, which are in whole or in part constructed of rubber which thereby require a different method of sterilization, such as heat sterilization, than the other components.

Moreover, although the use of a sealed can for containing the heat sterilized medicament agent vial has been specifically described, it will be apparent that any outer container for the vial that is impermeable to ethylene oxide would be suitable for the purpose. Thus, for example, such outer containers as aluminum foil or glass are contemplated as being useful for storing the medicament vial.

Having thus described the invention and the advantages thereof, it is considered that the invention is to be broadly construed and limited only by the character of the following claims.

I claim:

1. A medical procedure package comprising in combination:
   A. a sealed, pre-sterilized outer package wrap containing therein:
   B. an essentially unitary, two-compartment kit wrapped within an inner package wrap, said kit containing in the first of said compartments:
      (a) a medical procedure set-up tray and associated essential medical procedure components, said outer package wrap, set-up tray, essential medical procedure components and inner package wrap being compatible with ethylene oxide sterilization, and in the second of said compartments:
      (b) a medicament containing rubber closured vial contained within a sealed ethylene oxide impermeable container, said sealed container being also compatible with ethylene oxide sterilization, said vial and said container prior to sealing being sterilized by, and compatible with, heat sterilization, and said outer and inner package wraps, set-up tray, medical procedure components and vial-containing container being sterilized by ethylene oxide.

2. A medical procedure package according to claim 1 wherein said sealed container is a can equipped with a tear-off lid.

3. A medical procedure package according to claim 2 wherein said second compartment containing said sealed can is sealed with a peelable barrier over the top opening of said second compartment.

4. A medical procedure package according to claim 3 which is adapted for myelographic examination wherein said vial contains a myelographic radiopaque agent.

5. A medical procedure package according to claim 4 wherein said essential medical procedure components comprise scrubbing/cleansing means, local anesthesia producing means, local anesthetic injection means, sample/drug transfer means, drug injection means, fluid sampling means, patient covering means and swabbing/bandage means.

* * * * *